(12) United States Patent
Miller (10) Patent No.: US 7,451,766 B2
(45) Date of Patent: Nov. 18, 2008

(54) ENHANCED BREATHING DEVICE

(76) Inventor: Chipp St. Kevin Miller, 17765 Camino de Yatasto, Pacific Palisades, CA (US) 90272

( * ) Notice: Subject to any disclaimer, the term of this patent is extended or adjusted under 35 U.S.C. 154(b) by 950 days.

(21) Appl. No.: 10/816,566

(22) Filed: Apr. 1, 2004

(65) Prior Publication Data

US 2004/0194785 A1 Oct. 7, 2004

Related U.S. Application Data

(63) Continuation-in-part of application No. 10/405,782, filed on Apr. 1, 2003, now abandoned.

(51) Int. Cl.
*A61F 5/56* (2006.01)

(52) U.S. Cl. .................... 128/848; 128/207.15; 128/859

(58) Field of Classification Search ................. 128/846, 128/848, 859–862, 207.15
See application file for complete search history.

(56) References Cited

U.S. PATENT DOCUMENTS

| | | | |
|---|---|---|---|
| 4,170,230 A | | 10/1979 | Nelson |
| 4,185,639 A | * | 1/1980 | Linder .................... 128/200.26 |
| 4,256,099 A | * | 3/1981 | Dryden .................. 128/200.26 |
| 4,261,354 A | | 4/1981 | Nelson |
| 4,262,666 A | | 4/1981 | Nelson |
| 4,270,531 A | * | 6/1981 | Blachly et al. ......... 128/207.14 |
| 4,289,127 A | | 9/1981 | Nelson |
| 4,363,320 A | | 12/1982 | Kossove |
| 4,589,410 A | * | 5/1986 | Miller ..................... 128/207.15 |
| 4,821,715 A | | 4/1989 | Downing |
| 4,901,737 A | | 2/1990 | Toone |
| 4,919,126 A | | 4/1990 | Baildon |
| 5,117,816 A | | 6/1992 | Shapiro et al. |
| 5,443,063 A | | 8/1995 | Greenberg |
| 5,570,704 A | | 11/1996 | Buzzard et al. |
| 5,590,643 A | | 1/1997 | Flam |

(Continued)

OTHER PUBLICATIONS

International Search Report for corresponding application PCT/US04/10030 dated Nov. 19, 2004, 3pp.

(Continued)

*Primary Examiner*—Michael Brown
(74) *Attorney, Agent, or Firm*—Christie, Parker & Hale, LLP (57) ABSTRACT

An enhanced breathing device for use in a mouth of a user is provided that includes a flexible hollow tube having a proximal end, a distal end, an outer perimeter. The tube also includes an extraoral segment, and intraoral segment and an intermediate segment extending therebetween. The extraoral segment extends to the proximal end of the tube and includes at least one opening. The extraoral segment extends externally from the mouth of the user. The intraoral segment extends to the distal end of the tube and includes at least one opening. The intraoral segment extends into the mouth of the user and has a length sufficient for extending beyond a retromolar space, into the oropharynx and terminating between the posterior tongue and the soft palate. The intermediate segment has a length sufficient for extending along the buccopharyngeal pathway of the mouth of the user. The enhanced breathing device also includes a stop mounted on the tube to secure the intraoral segment within the oropharynx and to prevent a lengthwise movement of the tube relative to the mouth of the user.

53 Claims, 9 Drawing Sheets

U.S. PATENT DOCUMENTS

| | | |
|---|---|---|
| 5,727,564 A | 3/1998 | Yannalfo |
| 5,743,258 A | 4/1998 | Sato et al. |
| 5,868,138 A | 2/1999 | Halstrom |
| 5,921,241 A | 7/1999 | Belfer |
| 5,950,624 A | 9/1999 | Hart |
| 5,988,170 A | 11/1999 | Thomas |
| 6,041,784 A | 3/2000 | Halstrom |
| 6,161,542 A | 12/2000 | Halstrom |
| 6,263,877 B1 | 7/2001 | Gall |
| 6,269,816 B1 | 8/2001 | Rigonatti et al. |
| 6,386,199 B1 | 5/2002 | Alfery |
| 2001/0047805 A1 | 12/2001 | Scarberry et al. |
| 2002/0040712 A1 | 4/2002 | Chou |

OTHER PUBLICATIONS

Written Opinion for corresponding patent application PCT/US04/10030 dated Nov. 19, 2004, 3pp.

* cited by examiner

ENHANCED BREATHING DEVICE

CROSS-REFERENCE TO RELATED APPLICATION(S)

This application is a continuation-in-part of U.S. patent application Ser. No. 10/405,782, filed on Apr. 1, 2003 now abandoned.

FIELD OF THE INVENTION

The present invention relates generally to a enhanced breathing device for insertion into a user's mouth for providing an unobstructed buccopharyngeal pathway for inspiratory and expiratory airflow to enhance breathing, particularly during the sleep (to prevent snoring, sleep disordered breathing and/or obstructive sleep apnea) or sedation of the user.

BACKGROUND

Sleep Apnea is a common disorder affecting approximately 20,000,000 Americans. Sleep Apnea refers to a cessation of breathing during sleep that lasts at least 10 seconds. Snoring is another common sleep disorder. By conservative estimates, approximately 80,000,000 Americans are afflicted with snoring.

These sleep disorders cause countless hours of lost sleep and productivity for the afflicted persons, as well as their sleeping partners. In addition, Sleep Apnea is highly associated (50%) with essential hypertension, obesity and heart disease. Moreover, extreme cases of Sleep Apnea can be life threatening.

Current therapy includes sleep position modification, weight loss, and/or lifestyle changes such as the elimination of alcohol, drug use and/or over-eating. Other therapies include the use of mechanical devices such as oral or nasal devices that augment the airway, surgical procedures to enlarge and stabilize the airway during sleep, and continuous positive airway pressure devices.

Nasal devices that dilate the anterior nares by external traction or internal splinting have been used with minimal success. Nasal intubation is poorly tolerated and traumatic to the user.

Current oral devices are typically of two types. One type of oral device involves a tongue retention device that advances and secures the tongue using suction, or mechanical tongue depression and stabilization. However, this type of oral device has limited success and is poorly tolerated by the user. A second type of oral device is a mandibular repositioning device that advances the lower jaw relative to the fixed upper jaw to expand the cross-sectional area of the pharynx thereby improving airflow and preventing collapse. These devices have been variably effective, but commonly have both comfort and compliance problems.

Surgical treatments are varied and include reconstruction of the palate and uvula, various methods to shrink and stiffen the soft tissue of the upper airway, tonsillectomy, laser treatment, radio frequency tissue reduction, hyoid suspension, and tongue base excision and retention. More radical surgical treatments for severe disorders include tracheotomy and surgical advancement of the upper and lower jaws. Surgical treatments are typically highly expensive, painful, complicated and have varying success rates (typically 40-60%).

Nasal and/or oral continuous positive airway pressure has been the most successful of the current sleep disorder treatments. However, this treatment is highly expensive and poorly tolerated by many user's who typically find the treatment intrusive and intolerable. Accordingly, a need exists for an effective, well tolerated, economical treatment for persons afflicted with sleep disordered breathing.

There are approximately 31,000,000 outpatient surgeries and 40,000,000 inpatient surgical procedures performed annually in the United States. These procedures usually involve some form of anesthesia and sedation, which inherently requires airway management of the sedated patient. The airway is typically managed by an administrator such as the treating physician (M.D. or D.D.S.), an Anesthesiologist M.D. or a Certified Registered Nurse Anesthetist, among other appropriate administrators. The type of airway required for any given procedure is determined by safety considerations. In general, more deeply sedated and anesthetized patients require a more secure airway. The most secure airways involve endotracheal intubation with an airtight watertight seal within the tracheal lumen. Some procedures do not require a completely secure airway as patients may retain some of their protective reflexes in lighter stages of sedation. Alternative airways may be selected under these circumstances at the discretion of the administrator. Each airway type has intrinsic risks and the decision to use any particular airway is typically made by an analysis of the risk-benefit ratio for each individual patient. Accordingly, a need exists for an airway to facilitate the breathing of a sedated patient.

SUMMARY

In one embodiment, the present invention is an enhanced breathing device for use in a mouth of a user that includes a flexible hollow tube having a proximal end, a distal end, an outer perimeter. The tube also includes an extraoral segment, and intraoral segment and an intermediate segment extending therebetween. The extraoral segment extends to the proximal end of the tube and includes at least one opening. The extraoral segment extends externally from the mouth of the user. The intraoral segment extends to the distal end of the tube and includes at least one opening. The intraoral segment extends into the mouth of the user and has a length sufficient for extending beyond a retromolar space, into the oropharynx and terminating between the posterior tongue and the soft palate. The intermediate segment has a length sufficient for extending along the buccopharyngeal pathway of the mouth of the user. The enhanced breathing device also includes a stop mounted on the tube to secure the intraoral segment within the oropharynx and to prevent a lengthwise movement of the tube relative to the mouth of the user.

In another embodiment, the present invention is an enhanced breathing device for use in a mouth of a user that includes a flexible hollow tube having a proximal end, a distal end, an outer perimeter. The tube also includes an extraoral segment, and intraoral segment and an intermediate segment extending therebetween. The extraoral segment extends to the proximal end of the tube and includes at least one opening. The extraoral segment extends externally from the mouth of the user. The intraoral segment extends to the distal end of the tube and includes at least one opening. The intraoral segment extends into the mouth of the user and has a length sufficient for extending beyond a retromolar space, into the oropharynx and terminating between the posterior tongue and the soft palate. The intermediate segment has a length sufficient for extending along the buccopharyngeal pathway of the mouth of the user. The enhanced breathing device also includes an oxygen source having an outlet disposed in close proximity to the tube, allowing oxygen to flow from the outlet of the oxygen source to the tube.

In still another embodiment, the present invention is a method of creating a buccopharyngeal airway in a mouth of a user that includes providing a flexible hollow tube having a proximal end and a distal end. The method also includes positioning an extraoral segment of the tube, which extends to the proximal end of the tube and has at least one opening, exterior to the mouth of the user; positioning an intraoral segment of the tube, which extends to the distal end of the tube and has at least one opening, beyond a retromolar space in the mouth of the user, into the oropharynx and terminating between the posterior tongue and the soft palate; and positioning an intermediate segment of the tube, which extends between the extraoral and intraoral segments, along the buccopharyngeal pathway of the mouth of the user.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF EMBODIMENTS OF THE INVENTION

As shown in FIGS. 1A-7, embodiments of the present invention disclose an enhanced breathing device for insertion into a user's mouth for providing an unobstructed buccopharyngeal pathway for inspiratory and expiratory airflow to enhance breathing, particularly during the sleep (to prevent snoring, sleep disordered breathing and/or obstructive sleep apnea) or sedation of the user.

Snoring is a common benign condition characterized by noisy harsh breathing during sleep resulting from soft tissue airway collapse and vibration during the respiratory cycle. This creates a dynamic vibratory resonance between the pressure of respiratory effort and the inherent elastic recoil of the soft tissues. The enhanced breathing device of the present invention is used, in one embodiment, to displace the user's posterior tongue from the user's soft palate to reduce this dynamic vibratory resonance that results in snoring.

FIGS. 1A-7 show enhanced breathing devices 10A-10H that each include a flexible hollow tube 8 having three segments: an extraoral segment 14, an intraoral segment 18, and an intermediate segment 16 extending therebetween (hereinafter the enhanced breathing devices 10A-10H are generally referred to as the enhanced breathing device 10 unless a specific body is referenced.)

The extraoral 14 and intraoral 18 segments of the enhanced breathing device 10 each include at least one opening. In the depicted embodiments, the extraoral segment 14 includes an open end 20 and the intraoral segment 18 includes either a straight open end 21 (for example, see FIG. 1A) or an angled open end 21A (for example, see FIG. 1B).

Figure 3:
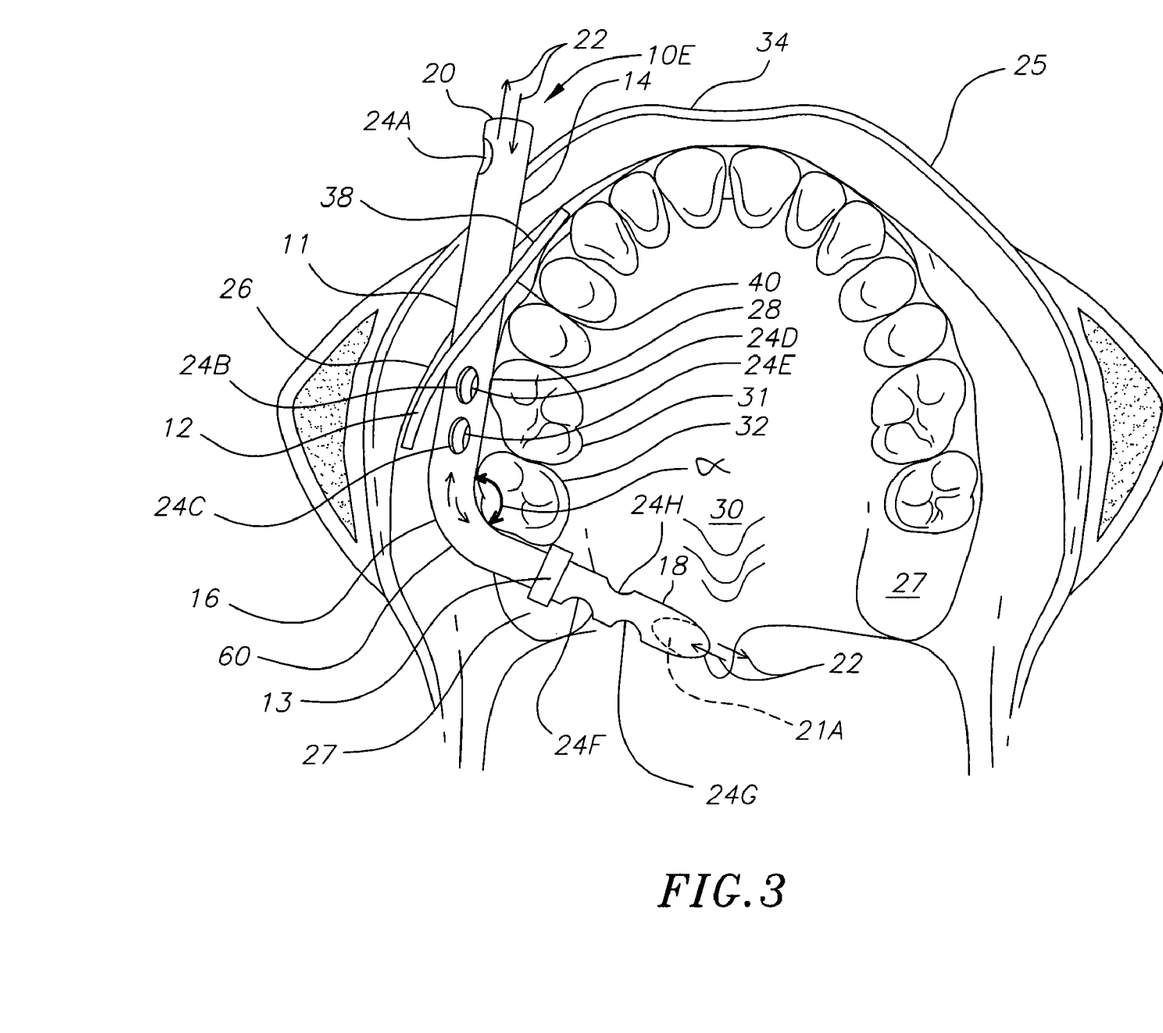
FIG. 3 is a cross-sectional view of the upper side of a user's mouth having an enhanced breathing device according to the present invention inserted therein.

As shown in FIG. 3, when the enhanced breathing device 10 is inserted into a user's mouth 25 a buccopharyngeal pathway 11 is created for inspiratory and expiratory airflow as illustrated by arrows 22. The buccopharyngeal pathway 11, as used herein, is defined as a pathway extending along an outer surface 28 of the user's dentition, between the outer surface 28 of the user's dentition and an inner surface 26 of the user's inner cheek, wherein dentition is defined as the teeth and gums in the user's dental arch.

When the enhanced breathing device 10 is positioned as shown in FIG. 3, the intraoral segment 18 extends along an outside of dentitions and around a rearmost dentition and past a retromolar space 27 (defined as an area in the user's upper or lower dentition past the user's last molar or an area past the user's upper and lower dentitions), enters the posterior oropharynx 30 (defined as the posterior oral cavity behind the user's dentition) and terminates between the posterior tongue and the soft palate. The retromolar space 27 as defined herein is created by the removal or nonexistence of at least the upper and/or lower third molar in the user's mouth 25.

In the embodiment of FIG. 3, the user's mouth contains a first upper molar 31 and a second upper molar 32, but does not contain a third upper molar. The absence of the third upper molar allows the enhanced breathing device 10 to cross behind the user's dentition and enter the user's posterior oropharynx 30. Although, the upper teeth are depicted, a depiction of the lower teeth would be substantially similar and is not included herein to avoid duplicity.

Adjacent to the intraoral segment 18 is the intermediate segment 16. In use, the intermediate segment 16 extends along the user's buccopharyngeal pathway 11. The intermediate segment 16 may be positioned adjacent to the user's upper dentition, lower dentition or both the upper and lower dentitions, and may pass through the retromolar space 27 in the user's upper dentition, lower dentition or both the upper and lower dentitions, as long as the intermediate segment 16 passes along the buccopharyngeal pathway 11 and the intraoral segment 18 enters the posterior oropharynx 30. The extraoral segment 14 is adjacent to the intermediate segment 16. The extraoral segment 14 extends past the user's lips 34 and outside the user's mouth 25.

When the enhanced breathing device 10 is positioned as described above, the unique buccopharyngeal pathway 11 is created as depicted by arrows 22 (see FIG. 3) for enhancing the inspiratory and expiratory airflow of the user. The buccopharyngeal pathway 11 is unique because it utilizes a route of airflow that is typically not used in normal breathing patterns and is not previously described in the medical literature as a route for respiratory airflow. The buccopharyngeal pathway 11 presents a pathway for airflow during normal breathing patterns only when it is "stented" open by the enhanced breathing device 10 as described above.

The enhanced breathing device 10 also allows for the buccopharyngeal pathway 11 to be stented open even when the user's mouth is closed and allows the user's dentition to remain in its natural and normal position, while accommodating normal jaw movement. As a result, normal swallowing, throat clearing, yawning, coughing and sneezing are not disturbed when the enhanced breathing device 10 is in the user's mouth. In addition, since the intraoral segment 18 is positioned in the posterior oropharynx 30 and terminates on the lateral-posterior tongue the naturally triggered gag reflex is markedly diminished.

The enhanced breathing device 10 is helpfully in reducing or eliminating snoring, sleep disordered breathing and obstructive sleep apnea for several reasons. For example, the intraoral segment 18 "stents" open or separates the posterior tongue and the soft tissue of the soft palate, which tend to collapse and vibrate during sleep to create the sound of snoring. The enhanced breathing device 10 also allows free flow of air to the posterior oral cavity at a markedly reduced resistance which allows for a decreased vacuum (negative) pressure of inspiration and a reduced pulsion (positive) pressure of expiration.

Figure 1A:
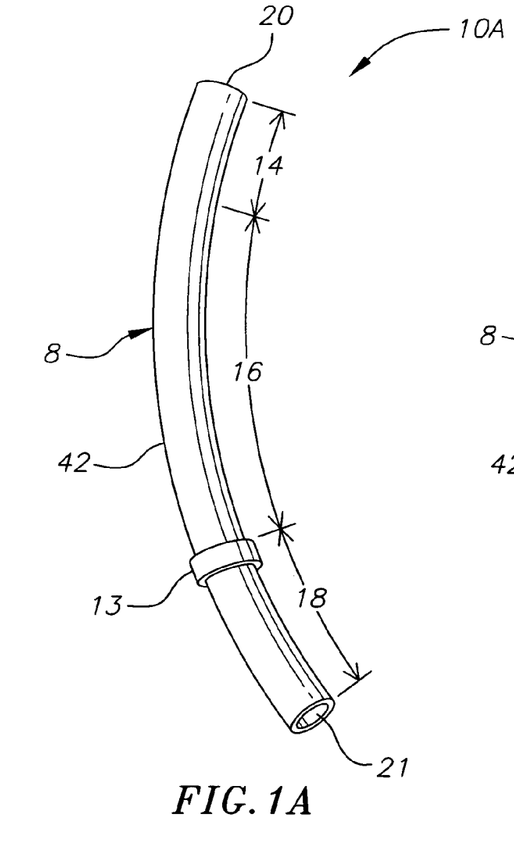
FIG. 1A is a front perspective view of one embodiment of an enhanced breathing device for enhancing breathing according to the present invention.
Figure 1B:
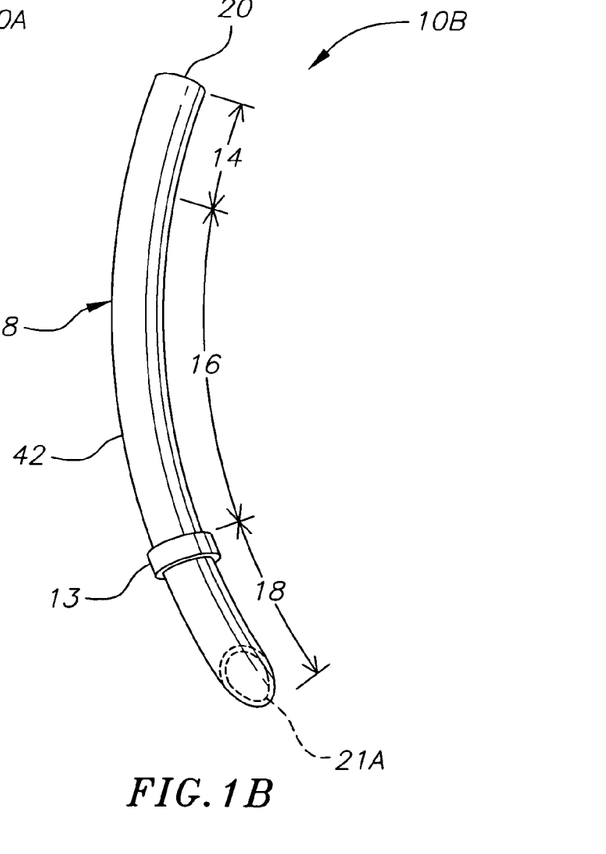
FIG. 1B is a front perspective view of another embodiment of an enhanced breathing device according to the present invention.
Figures 1C, 1D:
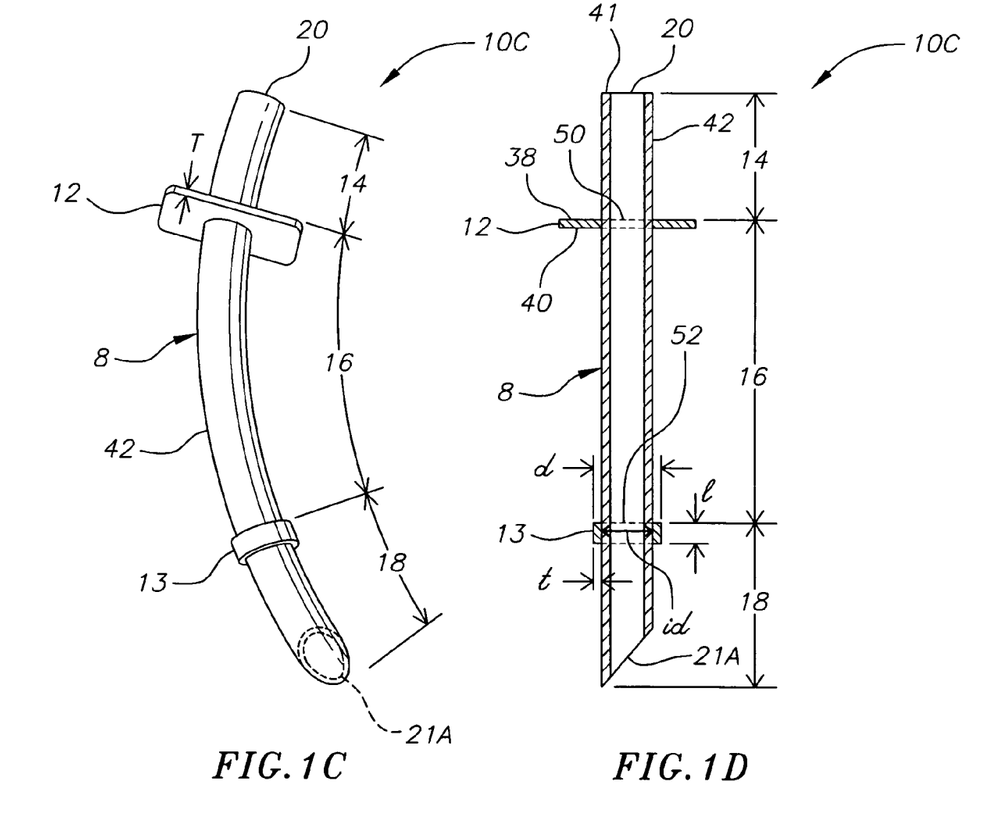
FIG. 1C is a front perspective view of another embodiment of an enhanced breathing device according to the present invention.
FIG. 1D is a cross-sectional side view of the enhanced breathing device of FIG. 1C.
Figures 2A, 2B:
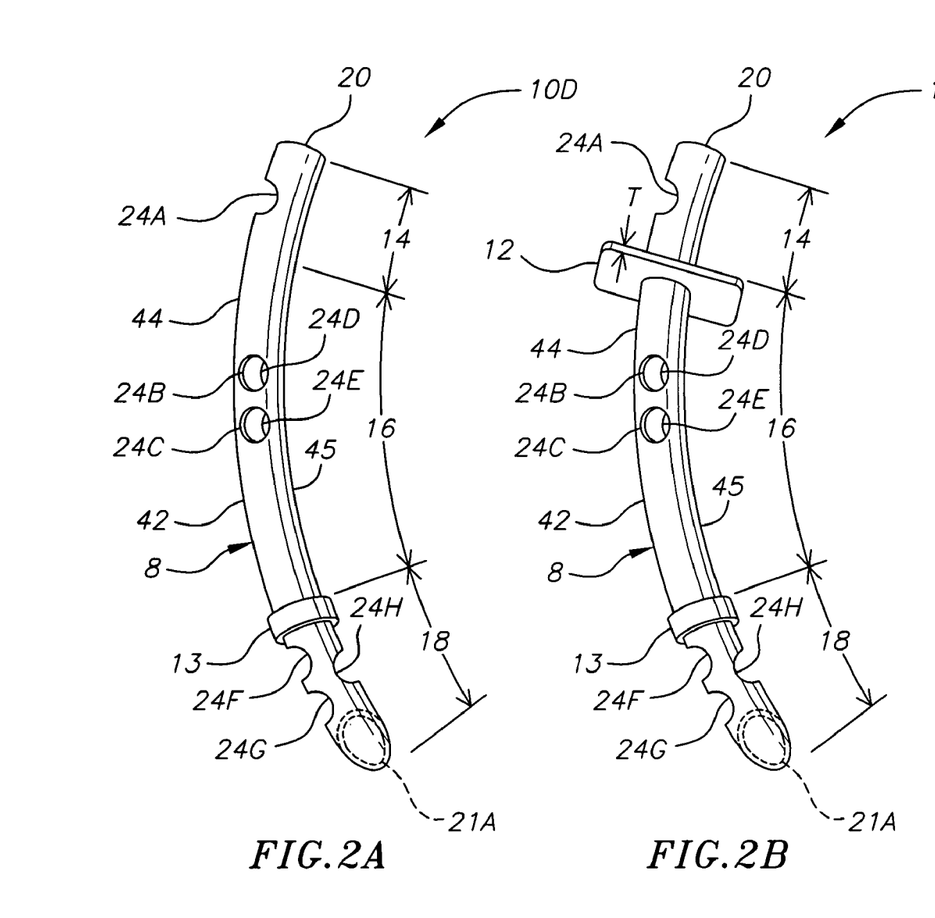
FIG. 2A is a front perspective view of another embodiment of an enhanced breathing device according to the present invention.
FIG. 2B is a front perspective view of another embodiment of an enhanced breathing device according to the present invention.
Figure 2C:
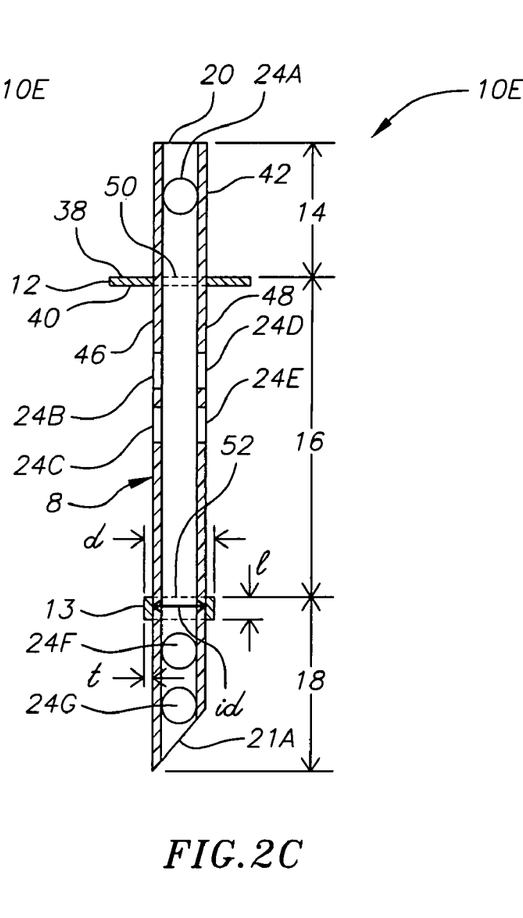
FIG. 2C is a cross-sectional side view of the enhanced breathing device of FIG. 2B.

As shown in FIGS. 1-3, the enhanced breathing devices 10A, 10B, 10C, 10D and 10E each contain a flexible outwardly extending stop 13 that forms a portion of the intraoral segment 18. In one embodiment, the stop 13 extends annularly about the tube 8. In another embodiment, the stop 13 extends from an outside diameter of the tube 8, but does not extend annularly about the tube 8. The stop 13 serves to secure the enhanced breathing device 10 against anterior displacement, and secures the intraoral segment 18 within the posterior oropharynx 30 of the user's mouth 25. The stop 13 is larger than the retromolar space 27 and therefore prevents retraction therethrough. The stop 13 frictionally secures the intraoral segment 18 within the posterior oropharynx 30 by abutting the last tooth in the retromolar space 27, which in the depicted embodiment is the second molar 32, and/or the portions of the jaw bone and/or gums that surround the retromolar space 27.

The stop 13 may be adjustable along the length of the tube 8, for example, by being slidably mounted on the outside diameter 42 of the tube 8. For example, in the embodiments shown in FIGS. 1-3, the stop 13 is a sleeve, that has an inner opening 52 (see FIGS. 1D and 2C) that is slightly smaller than or approximately equal to the outside diameter 42 of the tube 8. As a result, the stop 13 is frictionally secured to the tube 8, but can be adjusted along the outside diameter 42 of the tube 8 by the application of an appropriate force. The adjustability of the stop 13 allows the enhanced breathing device 10 to conform to the user's particular anatomy and allows for an adjustment of a length of the tube 8 that enters the posterior oropharynx 30.

The stop 13 may have any shape and size as long as it comfortably fits within the posterior oropharynx 30 of the user's mouth and secures the intraoral segment 18 within the posterior oropharynx 30 of the user's mouth 25. For example, in the embodiments shown in FIGS. 1-3, the stop 13 is a sleeve having concentric circular outside and inside surfaces, wherein the outside diameter d is approximately 28 French (Fr) to approximately 38 Fr, the inside diameter id is approximately 26 Fr to approximately 36 Fr, the length l is approximately 3/16 inch to approximately 1/2 inch and the thickness t is approximately 0.9 mm to approximately 7.5 mm, wherein 1 French is a unit of measure equal to 0.301 millimeters.

In one embodiment, the stop 13 has an outside diameter d of approximately 32 Fr, an inside diameter id of approximately 28 Fr, a length l of approximately 1/4 inch, a thickness t of approximately 1.2 mm and the tube 8 has an outside diameter 42 of approximately 28 Fr.

As shown in FIGS. 1C-1D and 2B-3, the enhanced breathing devices 10C and 10E each contain a thin flexible retention diaphragm 12. In the embodiment of FIG. 3, for example, the retention diaphragm 12 contains a first side 38 that, due to its flexibility, conforms to the user's inner lips and/or inner cheek and a second side 40 that conforms to an outer surface of the user's teeth. In this embodiment, the retention diaphragm 12 secures the intermediate segment 16 within the user's buccopharyngeal pathway 11 and prevents anterior displacement of the enhanced breathing device 10. The retention diaphragm 12 also acts as a saliva dam to prevent drooling of naturally occurring saliva developed by the user during sleep or sedation.

The retention diaphragm 12 is adjustable, for example, by being slidably mounted to the outside diameter 42 of the tube 8. For example in one embodiment, the retention diaphragm 12 includes an opening 50 (see FIGS. 1D and 2C) that is slightly smaller than or equal to the outside diameter 42 of the tube 8. As a result, the retention diaphragm 12 is frictionally secured to the tube 8, but can be adjusted along the outside diameter 42 of the tube 8 by the application of an appropriate force. The adjustability of the retention diaphragm 12 allows the enhanced breathing device 10 to conform to the user's particular anatomy.

The retention diaphragm 12 may have any shape and size. However, in embodiments where the retention diaphragm 12 is used intraorally, it is desirable for the retention diaphragm 12 to be sized and shaped to fit comfortably within the user's mouth between the user's inner lips and/or inner cheek and an outer surface of the user's teeth. In the embodiment of FIG. 3, the retention diaphragm 12 has a square outer perimeter or shape, having sides that are approximately 3/4 inch to approximately 1 1/2 inch. The square shape helps to prevent rotation of the device 10 when it is intraorally positioned as described above. However, in other embodiments, the retention diaphragm 12 may be circular, rectangular, square, oval-shaped, or any other suitable shape.

In the embodiments of FIGS. 1C-1D, 2B-3, the retention diaphragm 12 has an outer perimeter that is square having 1 inch sides, wherein the opening 50 (see FIGS. 1D and 2C) is circular with a diameter of approximately 28 Fr and the tube 8 has an outside diameter 42 of approximately 28 Fr. In the embodiments of FIGS. 1C-1D, 2B-3, the retention diaphragm 12 has a thickness T of approximately 0.030 inches to approximately 0.060 inches.

In the embodiment of FIGS. 2A-2C, the extraoral segment 14, the intermediate segment 16, and the intraoral segment 18 each contain side openings or side ventilation openings 24A-24G. The ventilation openings 24A-24G serve to maximize airflow that may be restricted, for example by pillows, bed sheets or other objects obstructing the open end 20 of the extraoral segment 14 and/or soft tissue or other objects obstructing the open end 21 or 21A of the intraoral segment 18.

For added ergonomic effect and comfort, and for proper fitting in the user's mouth, the enhanced breathing device 10, in the embodiments of FIGS. 1A-3, has a preformed bend such that a convex side 44 of the tube 8 and an opposite concave side 45 of the tube 8 are curved to closely follow the shape of a typical user's dentition. For example, in one embodiment the bend approximates an arc of a circle having a radius in the range of approximately 2.5 inches to approximately 5.0 inches, such as 4.0 inches.

In the depicted embodiments, the ventilation openings 24A-24G are circular in shape with a diameter of approximately 5.0 mm. In the embodiments depicted in FIGS. 2A-3, the extraoral segment 14 contains one ventilation opening 24A disposed on the convex side 44 of the tube 8; the intermediate segment 16 contains two ventilation openings 24B and 24C disposed on an upper 46 side of the tube 8 (between the convex 44 and concave 45 sides of the tube 8) and two ventilation openings 24D and 24E disposed on a lower 48 side of the tube 8 (opposite the upper side 46 of the tube 8); and the intraoral segment 18 contains two ventilation openings 24F and 24G disposed on the convex side 44 of the tube 8 and one ventilation opening 24H disposed on the concave side 45 of the tube 8.

Although specific sizes and shapes are discussed above, the ventilation openings 24A-24G may have any size and any shape, such as square, rectangular, triangular, oval-shapes or diamond shapes among other appropriate shapes. In addition, the extraoral segment 14, the intermediate segment 16 and the intraoral segment 18 may each contain any number of ventilation openings 24A-24G as long as the ventilation openings 24A-24G allow airflow to enter into the tube 8 and allow sufficient airflow through the tube 8 during instances when the extraoral opening 20 and/or the intraoral opening 21 or 21A is obstructed. The ventilation openings 24A-24G may also be disposed on the tube 8 at positions other than that shown in FIGS. 2A-3. However, the positions shown in FIGS. 2A-3 minimizes the likelihood of the ventilation openings 24A-24G being obstructed.

For example, as shown in FIG. 3, positioning ventilation openings in the convex side 44 of the extraoral segment 14 minimizes the likelihood of the user's outer lips obstructing the ventilation openings in the extraoral segment 14 since the user's lips are adjacent to the concave side 45 of the tube 8 when the enhanced breathing device 10 is in use. Positioning ventilation openings between the convex 44 and concave 45 sides in the upper 46 and/or lower 48 sides of the intermediate segment 16 minimizes the likelihood of the inner surface 26 of the user's inner cheek and/or the outer surface 28 of the user's dentition obstructing the ventilation openings in the intermediate segment 16. Positioning ventilation openings in the concave 45 and the convex 44 sides of the intraoral segment 18 minimizes the likelihood of the user's tongue or soft palate obstructing the ventilation openings in the intraoral segment 18.

The preformed bend of the enhanced breathing device 10, having the convex 44 and the concave 45 sides that are curved to closely follow the shape of a typical user's dentition, facilitates properly inserting the enhanced breathing device 10 into the user's mouth and ensures that when the enhanced breathing device 10 is inserted properly, the ventilation openings 24A-24G are properly aligned within the user's mouth to minimize the likelihood of any of the ventilation openings 24A-24G being obstructed. However, as shown in FIG. 3, when the user positions the intraoral segment 18 beyond the retromolar space 27 in the user's mouth, into the posterior oropharynx 30 between the posterior tongue and the soft palate, the intraoral segment 18 may bend inwardly more sharply than the preformed bend in order to properly place the enhanced breathing device 10 within the user's mouth. In one embodiment, the above described preformed bend contains an additional inward bend 60 near the junction of the intermediate 16 and intraoral 18 segments as shown in FIG. 3. The inward bend 60 is bent at an angle $\alpha$ in the range of approximately 65 degrees to 135 degrees, such as 100 degrees.

In the embodiment of FIG. 1A, the open end 21 of the intraoral segment 18 is cut straight across the tube 8, i.e. approximately straight across from the upper side 46 of the tube 8 to a lower side 48 of the tube 8. In the embodiments of FIGS. 1B-3, the open end 21A of the intraoral segment 18 is angled starting from the upper side 46 of the tube 8 to a lower side 48 of the tube 8. In one embodiment, this angle is approximately 45 degrees, however, in other embodiments larger or smaller angles may be used. The angled open end 21A of the intraoral segment 18 facilitates insertion of the intraoral segment 18 into the retromolar space 27. In addition, the angled open end 21A of the intraoral segment 18 makes it less likely for the tongue or the soft palate to obstruct the open end 21A when the enhanced breathing device 10 is in a user's mouth.

In one embodiment, the tube 8 has a predetermined length of approximately 9 cm to approximately 13 cm. Although other lengths may be used, when the tube length is longer than 15 cm the extraoral segment 14 can extend too far from the typical user's mouth, which may cause the extraoral segment 14 to bind or become obstructed, and when the tube length is shorter than 9 cm the tube 8 is not long enough for both the extraoral segment 14 to extend from the user's mouth and the intraoral segment 18 to extend into the posterior oropharynx 30 of the user's mouth for a typical user. In one embodiment, the tube 8 has a length of 12 cm.

In one embodiment, the tube 8, the retention diaphragm 12 and the stop 13 are each composed of a flexible, elastic material, such as a non-latex polyvinyl chloride material. When the enhanced breathing device 10 is composed of a flexible, elastic material, it is allowed to negotiate the contours of the user's buccopharyngeal pathway 11 while maintaining user comfort. In addition, the flexibility and elasticity of the enhanced breathing device 10 allows for a compression of the enhanced breathing device 10 during normal functions during sleep or sedation, such as swallowing and teeth clenching, while allowing the enhanced breathing device 10 to regain its original dimension when those forces are relieved.

In the depicted embodiments, the outside diameter 42 of the tube 8 is approximately 26 Fr to approximately 36 Fr, the inside diameter 43 of the tube is approximately 23 Fr to approximately 33 Fr, and the thickness 41 of the tube 8 is approximately 1.0 mm to approximately 2.5 mm. In one embodiment, the outside diameter 42 of the tube 8 is approximately 28 Fr, the inside diameter 43 of the tube 8 is approximately 25 Fr and the thickness 41 of the tube 8 is approximately 1.0 mm.

The outside diameter 42 of the tube 8 may be larger than 36 Fr, but at diameters larger than 36 Fr user comfort begins to decrease. The inside diameter 43 of the tube 8 may be smaller than 26 Fr, but sufficient airflow begins to diminish at 26 Fr. The thickness 41 of the tube 8 may be smaller than 0.9 mm or larger than 2.5 mm, but at smaller thicknesses the device 10 becomes too flimsy and a larger thicknesses the device 10 becomes too stiff. In one embodiment, all of the outer edges of the tube 8, the retention diaphragm 12 and the stop 13 are rounded to avoid abrasion or irritation of the user's soft tissue when the enhanced breathing device is in a user's mouth.

Figure 3A:
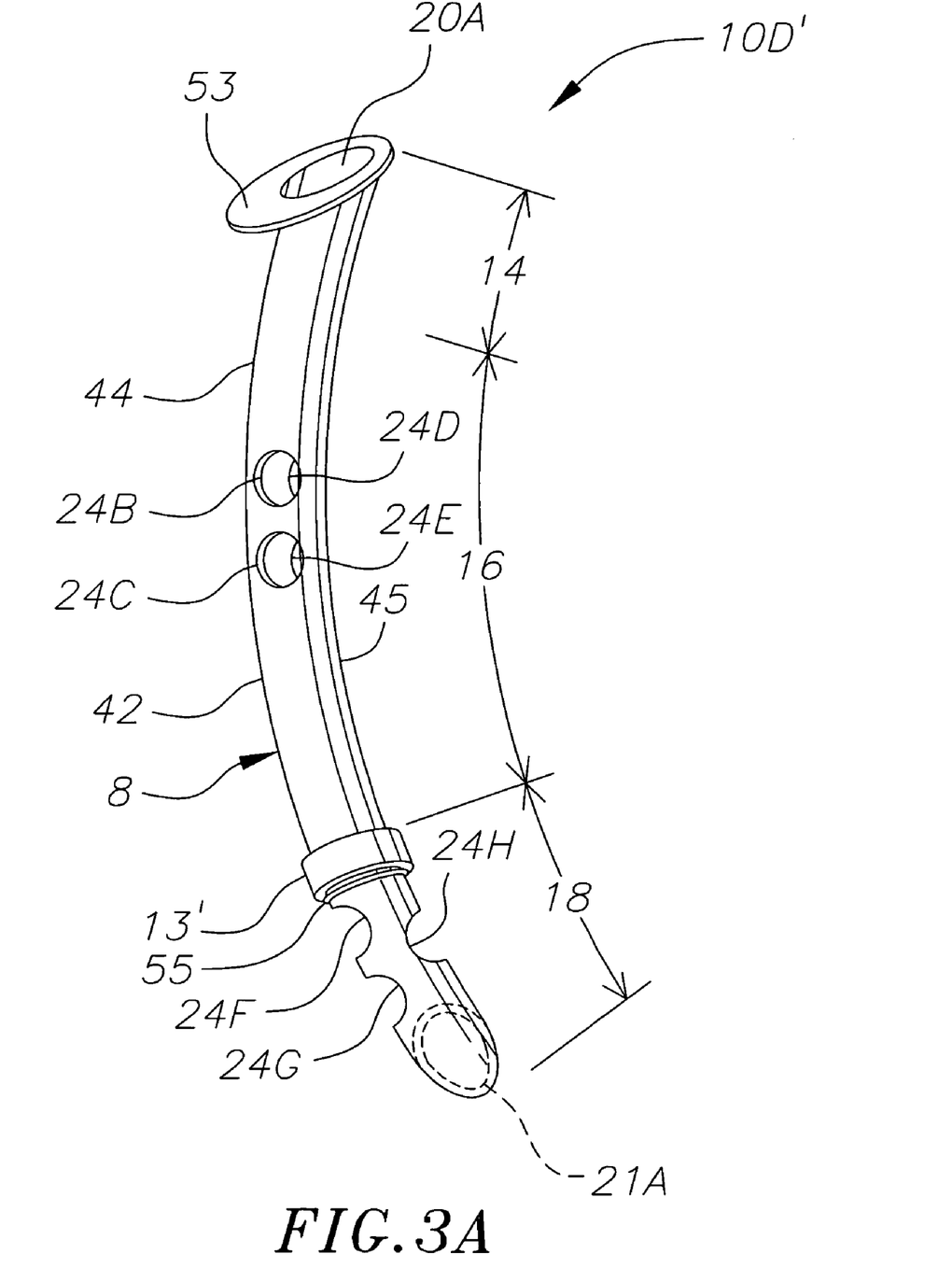
FIG. 3A is a front perspective view of another embodiment of an enhanced breathing device according to the present invention.

FIG. 3A shows an enhanced breathing device 10D' similar to that described above with respect to the enhanced breathing device 10D of FIG. 2A, including the tube 8, with the extraoral 14, intermediate 16 and extraoral 18 segments, the ventilation openings 24B-24H (although the ventilation opening 24A is omitted from this embodiment it could be included in an alternative to this embodiment.), and the stop 13. The enhanced breathing device 10D' of FIG. 3A also includes an angled open end 20A on the extraoral segment 14 of the tube 8; a flange 53 adjacent to the angled open end 20A; and an extension 55 for limiting a movement of the stop 13 in a lengthwise direction towards the end 21A of the intraoral segment 18 of the tube 8.

Angling the open end 20A of the extraoral segment 14 of the tube 8 allows the end 20A of the extraoral segment 14 to more closely mimic the curvature of the outer lips of the user. The flange 53 creates a visually appealing end to the extraoral segment 14. In addition, the flange 53 helps prevent an unintentional swallowing of the tube 8 by the user. The flange 53 and the extension 53 (described in more detail below) may be integrally formed with the tube 8 or separately mounted thereto.

The extension 55 extends from the outer diameter of the tube 8 and functions to prevent a distal movement of the stop 13 therepast. As such, the extension 55 prevents the stop 13 from inadvertently sliding off of the end 21A of the intraoral segment 18 of the tube 8. In the depicted embodiment, the extension 55 is positioned between the stop 13 and the ventilation openings 24F-24H to prevent the stop from obstructing the ventilation openings 24F-24H. Any of the embodiments described above may include the angled open end 20A, the flange 53 and/or the extension 55 as described above and shown in FIG. 3A.

Figure 4:
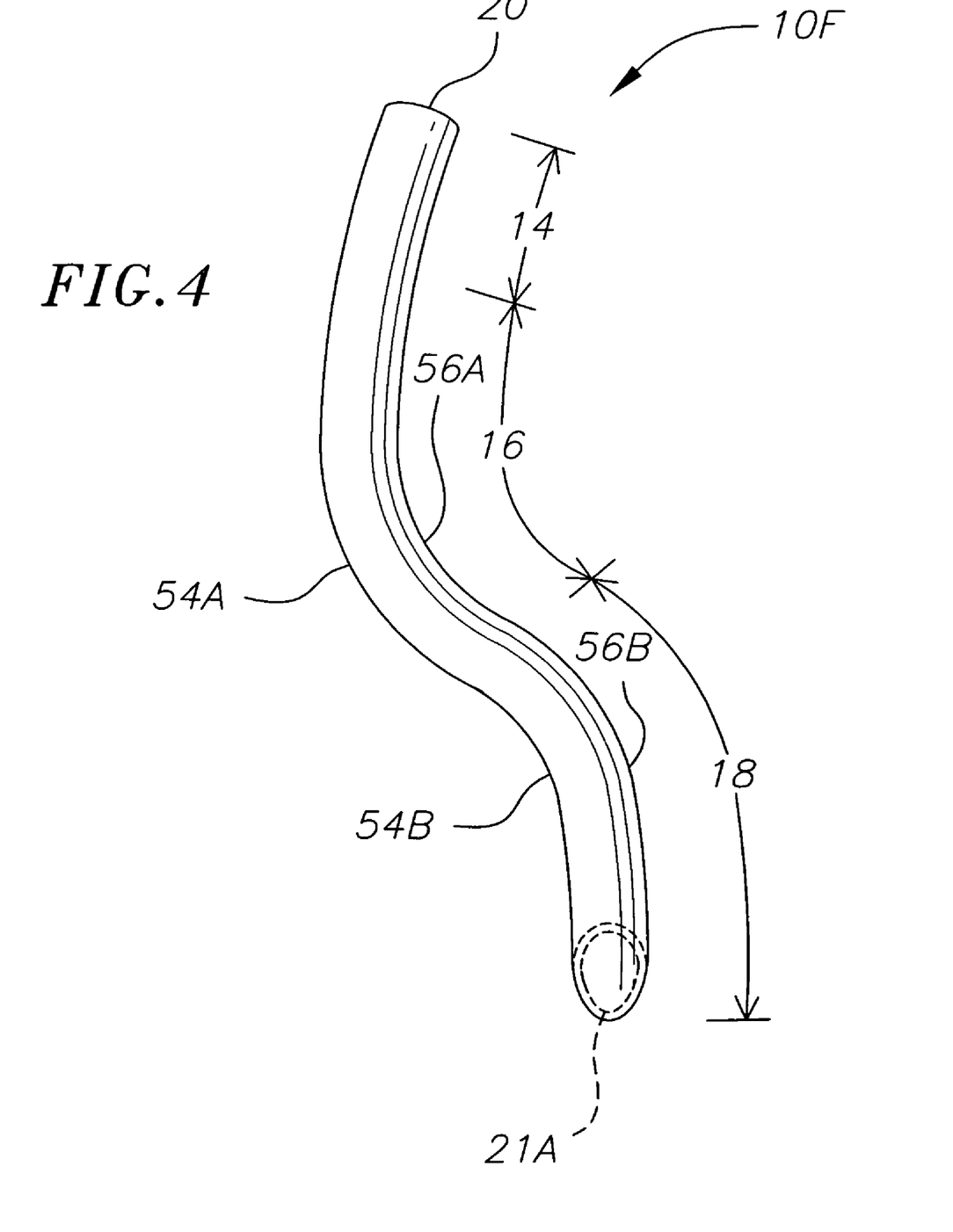
FIG. 4 is a front perspective view of another embodiment of an enhanced breathing device according to the present invention.

Any of the embodiments described above may include the preformed shape of the enhanced breathing device 10F as shown in FIG. 4. In the preformed shape of FIG. 4, the tube 8 includes a first concave surface 54A and an opposite first convex surface 56A that each integrally adjoin, respectively, a second convex surface 54B and an opposite second concave surface 56B, such that the tube 8 is approximately "S-shaped". In one embodiment, the first concave surface 54A and the first convex surface 56A are disposed on the extraoral 14 and intermediate 16 segments and the second convex surface 54B and the second concave surface 56B are disposed 16 on the intraoral segment 18.

Figures 5A, 5B:
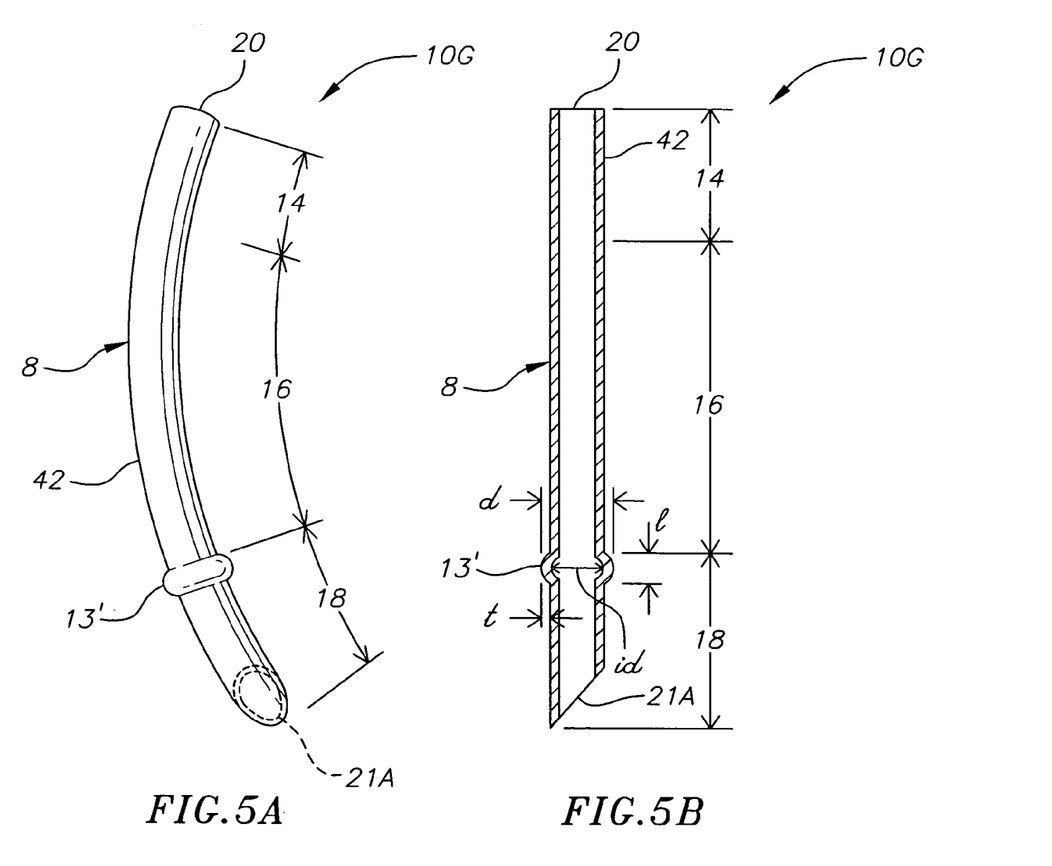
FIG. 5A is a front perspective view of another embodiment of an enhanced breathing device according to the present invention.
FIG. 5B is a cross-sectional side view of the enhanced breathing device of FIG. 5A

Any of the embodiments described above may include the stop 13' of the enhanced breathing device 10G as shown in FIGS. 5A-5B. In the enhanced breathing device 10G, the stop 13' is formed as a preformed expansion in the tube 8, integrally formed with the tube 8, and extending from the outside diameter 42 of the tube 8. In one embodiment, the stop 13' extends annularly about the tube 8. In another embodiment, the stop 13' extends from the outside diameter of the tube 8, but does not extend annularly about the tube 8. In this embodiment, the stop 13' is not movable relative to the tube 8.

In one embodiment, the dimensions of the stop 13' when formed as a preformed expansion in the tube 8 (the outer diameter d, the inside diameter id, the length l, and the thickness t) are approximately the same as the dimensional ranges given above in the embodiments where the stop 13 is a sleeve.

For some medical procedures, during and/or after the sedation of a patient, oxygen is delivered to the patient. Any of the enhanced breathing devices 10A-10H disclosed herein may be used to facilitate the delivery of oxygen to a patient during and/or after the sedation of a patient.

Figures 6A, 6B:
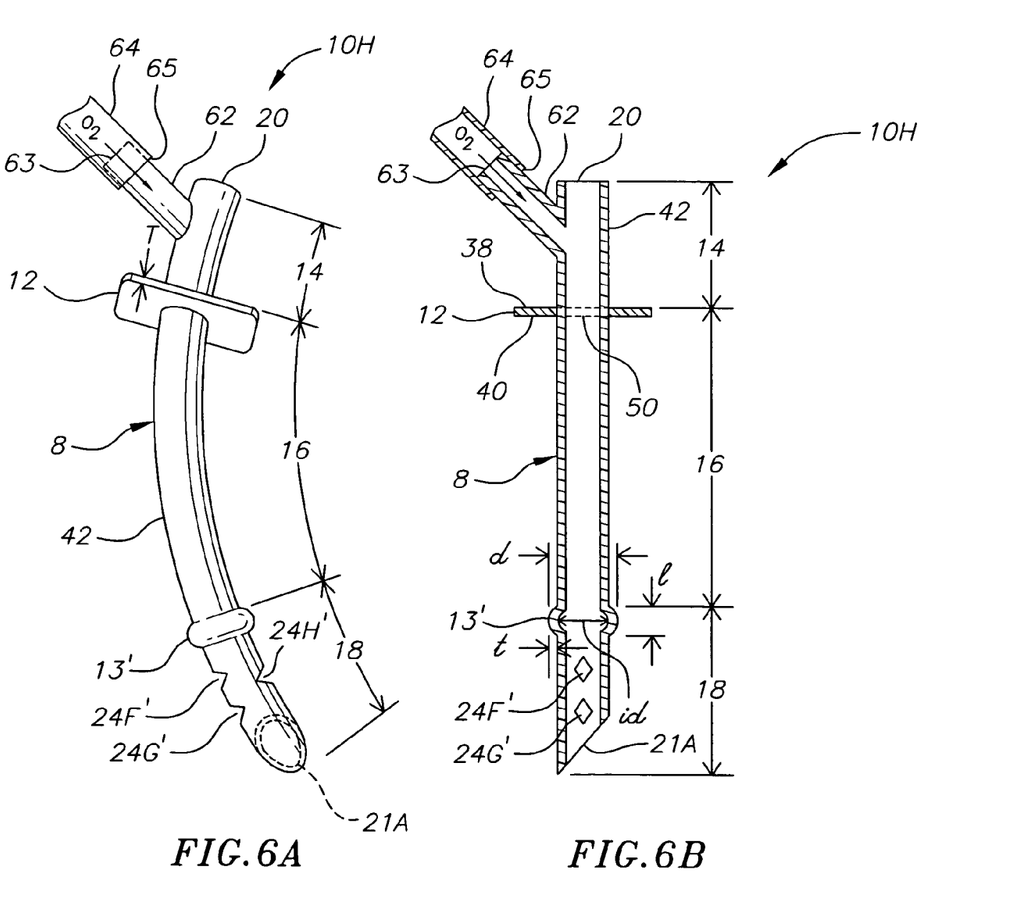
FIG. 6A is a front perspective view of another embodiment of an enhanced breathing device according to the present invention connected to an oxygen source (shown schematically)
FIG. 6B is a cross-sectional side view of the enhanced breathing device and oxygen source of FIG. 6A.

Any of the embodiments described above may include a connector stem 62, as shown in the enhanced breathing device 10H of FIGS. 6A and 6B. The connector stem 62 is removably connected to an oxygen source 64 (shown schematically in FIGS. 6A and 6B.) The oxygen source 64 may be any known device used for supplying oxygen to a patient, such as an oxygen tank. The oxygen source 64 provides oxygen ($O_2$) to an inlet 63 of the connector stem 62, allowing oxygen to enter the tube 8, traverse the buccopharyngeal pathway created by the tube 8, exit the tube 8 in the posterior oropharynx, and thereby facilitate the inspiration of the oxygen by the patient.

In the embodiment of FIGS. 6A-6B, an outlet 65 of the oxygen source 64 has an inner perimeter that is smaller than or approximately equal to an outer perimeter of the inlet 63 of the connector stem 62. As such, the outlet 65 of the oxygen source 64 connects to the inlet of the connector stem 62 in a frictional engagement. In this embodiment, the connector stem 62 is integrally formed with the tube 8 and is formed of a flexible, compressible, elastic material, such as a non-latex polyvinyl chloride material. The compressibility of this material allows for the frictional engagement of the outlet 65 of the oxygen source 64 with the inlet 63 of the connector stem 62. In other embodiments, however, the oxygen source 64 may be connected to the connector stem 62 by any known means as long as the connection allows oxygen to flow from the outlet 65 of the oxygen source 64 to the inlet 63 of the stem 62. Alternatively, the outlet 65 of the oxygen source 64 may be connected directly to the open end 20 of the extraoral segment 14 of the tube 8

In the embodiment of FIGS. 6A and 6B, the connector stem 62 is cylindrically shaped and connects to the extraoral segment 14 of the tube 8 at an angle. However, in other embodiments, the connector stem 62 may have any appropriate size or shape and may be connected to the tube 8 at any angle as long as oxygen is allowed to transverse the connector stem 62 and enter the tube 8.

In use, the connector stem 62 extends extraorally and the retention diaphragm 12 extends either intraorally as described above, or extraorally. Placing the retention diaphragm 12 extraorally prevents posterior displacement of the tube 8 and allows a person who is monitoring the patient to detect any movement of the tube 8. The retention diaphragm 12 may have the dimensions described above. However, in embodiments where the retention diaphragm 12 is intended to be used extraorally, the size of the retention diaphragm 12 can be larger than that described above since user comfort is less of a concern when the retention diaphragm 12 is used extraorally.

When the enhanced breathing device 10 is used to receive oxygen during or after the sedation of a patient, the enhanced breathing device 10 may contain any or all of the side ventilation openings 24A-24H as described above and depicted for example in FIGS. 2A-3. However, in the embodiment of FIGS. 6A and 6B, the enhanced breathing device 10 only includes side ventilation openings in the intraoral segment 18. This allows oxygen from the oxygen source 64 to be guided directly to the posterior oropharynx 30 to facilitate inspiration of the oxygen by the user. Although, the intraoral segment 18 may include any number and shape of ventilation openings, in the embodiment of FIGS. 6A and 6B, the intraoral segment 18 includes three diamond shaped ventilation openings 24F'-24H' positioned as described above for the ventilation openings 24F-24H as shown in FIGS. 2A-3.

Figure 7:
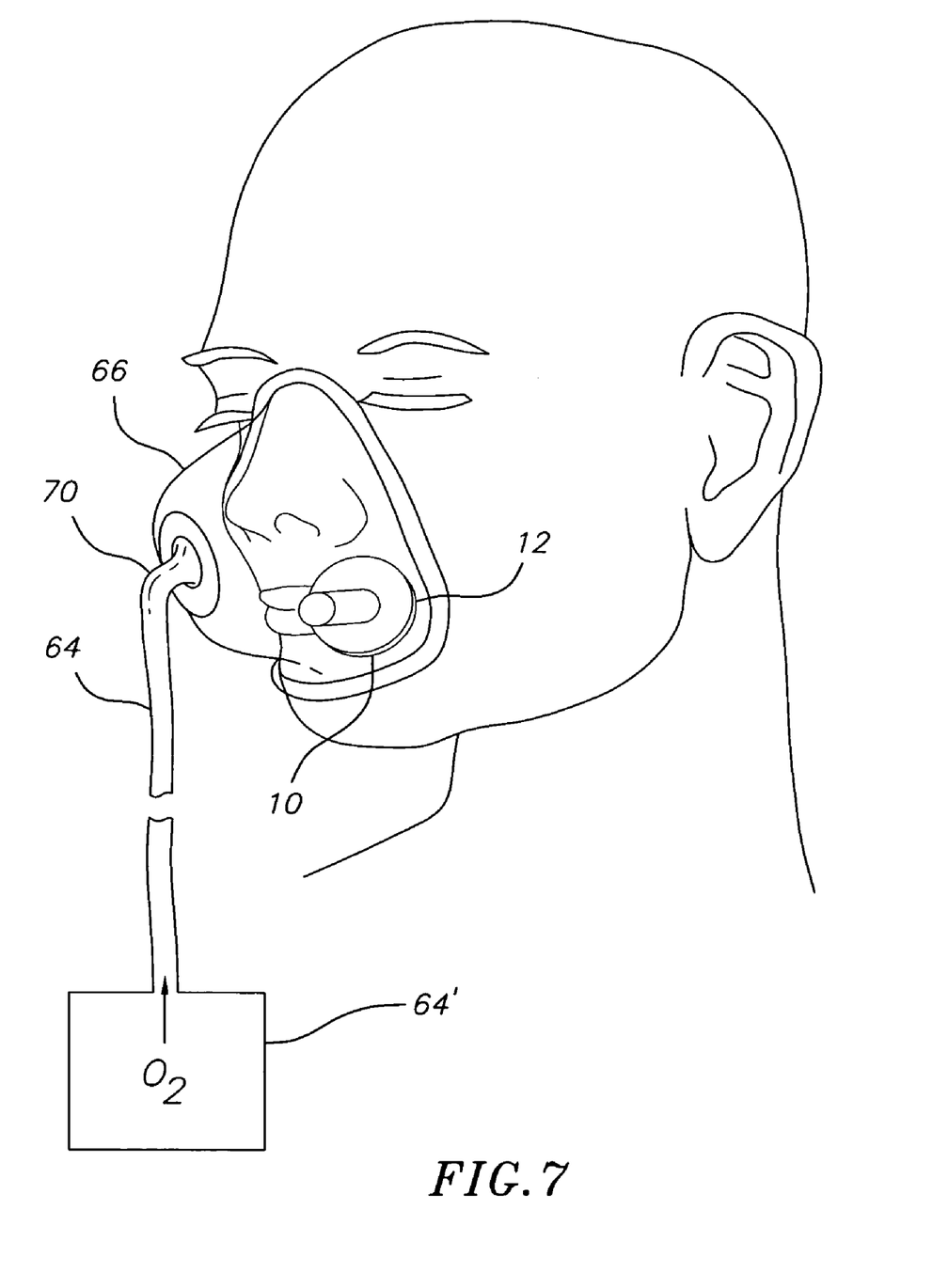
FIG. 7. is a perspective view of an enhanced breathing device according to one embodiment of the invention being used in conjunction with an oxygen mask.

In the embodiment of FIG. 7, the oxygen source 64' (shown schematically), is connected to an oxygen mask 66 via a conduit 68. The conduit 68 receives oxygen from the oxygen source 64', such as an oxygen tank, and directs the received oxygen through an outlet 70 of the conduit 68 and into the oxygen mask 66. The oxygen mask 66 is disposed in surrounding relation to the enhanced breathing device 10, such that the received oxygen from the oxygen source 64 enters the enhanced breathing device 10 and is inspired by the user (for clarity it is noted here that the enhanced breathing device 10 shown in FIG. 7, may be any of the above described enhanced breathing devices 10A-10H.) It is also to be understood that the oxygen source 64 and mask 66 is not limited by that which is shown in FIG. 7, and may be any known oxygen source and mask, connected to the face of the user by any known means.

The preceding description has been presented with reference to various embodiments of the invention. Persons skilled in the art and technology to which this invention pertains will appreciate that alterations and changes in the described structures and methods of operation can be practiced without meaningfully departing from the principle, spirit and scope of this invention. Accordingly, the foregoing description should not be read as pertaining only to the precise structures described and shown in the accompanying drawings, but rather should be read as consistent with and as support for the following claims, which are to have their fullest and fairest scope.

The invention claimed is:

1. An enhanced breathing device for use in a mouth of a user and comprising:
   a flexible hollow tube comprising a proximal end, a distal end, an outer perimeter, and further comprising:
      an extraoral segment extending to the proximal end of the tube and comprising at least one opening, wherein the extraoral segment extends externally from the mouth of the user;
      an intraoral segment extending to the distal end of the tube and comprising at least one opening, wherein the intraoral segment extends into the mouth of the user and comprises a length sufficient for extending beyond a retromolar space, into the oropharynx and terminating between the posterior tongue and the soft palate; and
      an intermediate segment extending between the extraoral and intraoral segments and comprising a length sufficient for extending along an outside of dentitions of the user and around a rearmost dentition of the user to create a buccopharyngeal pathway of the mouth of the user; and
   a stop on the intraoral segment to secure the intraoral segment within the oropharynx against movement of the tube out of the mouth of the user.

2. The enhanced breathing device of claim 1, wherein the stop abuts a rear molar in the mouth of the user.

3. The enhanced breathing device of claim 1, wherein the stop comprises an outer perimeter that is larger than the retromolar space and the outer perimeter of the tube is smaller than the retromolar space.

4. The enhanced breathing device of claim 1, wherein the stop is adjustable lengthwise along the tube.

5. The enhanced breathing device of claim 1, wherein the stop is slidably movable along the outer perimeter of the tube.

6. The enhanced breathing device of claim 1, further comprising an extension from the outer perimeter of the tube that prevents a distal movement of the stop therepast.

7. The enhanced breathing device of claim 6, wherein the extension is on the intraoral segment of the tube.

8. The enhanced breathing device of claim 1, wherein the distal end of the tube is angled to facilitate insertion of the intraoral segment into the retromolar space.

9. The enhanced breathing device of claim 1, wherein the tube comprises an outer preformed bend having a convex side and an opposite concave side.

10. The enhanced breathing device of claim 9, wherein the extraoral segment comprises an open end; the intraoral segment comprises an open end and at least one ventilation opening disposed on at least one of the convex side and the concave side of the tube; and the intermediate segment contains at least one ventilation opening disposed on at least one of an upper side between the convex and concave sides of the tube and an opposite lower side of the tube.

11. An enhanced breathing device for use in a mouth of a user and comprising:
    a flexible hollow tube comprising a proximal end, a distal end, an outer perimeter, and further comprising:
       an extraoral segment extending to the proximal end of the tube and comprising at least one opening, wherein the extraoral segment extends externally from the mouth of the user;
       an intraoral segment extending to the distal end of the tube and comprising at least one opening, wherein the intraoral segment extends into the mouth of the user and comprises a length sufficient for extending beyond a retromolar space, into the oropharynx and terminating between the posterior tongue and the soft palate; and
       an intermediate segment extending between the extraoral and intraoral segments and comprising a length sufficient for extending along a buccopharyngeal pathway of the mouth of the user;
    a stop on the tube to secure the intraoral segment within the oropharynx against movement of the tube out of the mouth of the user; and
    a retention diaphragm slidably mounted on the tube for securing the intermediate segment within the user's buccopharyngeal pathway.

12. The enhanced breathing device of claim 1, wherein the tube has a preformed outer shape comprising a first portion with a first concave surface and an opposite first convex surface and a second portion with a second convex surface and an opposite second concave surface.

13. The enhanced breathing device of claim 1, wherein the stop is formed as a preformed expansion in the tube.

14. The enhanced breathing device of claim 1, further comprising an oxygen source comprising an outlet disposed in close proximity to the tube, allowing oxygen to flow from the outlet of the oxygen source to the tube.

15. The enhanced breathing device of claim 14, wherein the outlet of the oxygen source is connected to the extraoral segment.

16. The enhanced breathing device of claim 14, wherein the tube comprises a connector stem that removably connects to the outlet of the oxygen source.

17. The enhanced breathing device of claim 14, wherein an end of the oxygen source is disposed in surrounding relation to the extraoral segment of the tube.

18. The enhanced breathing device of claim 14, wherein the outlet of the oxygen source is connected to a mask that is disposed in surrounding relation to the extraoral segment of the tube.

19. The enhanced breathing device of claim 1, wherein the extraoral segment comprises an open end and wherein the intraoral segment comprises an open end.

20. The enhanced breathing device of claim 19, wherein the open end of the intraoral segment is angled starting from an upper side of the tube to a lower side of the tube.

21. The enhanced breathing device of claim 19, wherein the intraoral segment comprises at least one ventilation opening.

22. The enhanced breathing device of claim 21, wherein the intermediate segment comprises at least one ventilation opening.

23. The enhanced breathing device of claim 22, wherein the extraoral segment comprises at least one ventilation opening.

24. An enhanced breathing device for use in a mouth of a user and comprising:
    a flexible hollow tube comprising a proximal end, a distal end, an outer perimeter, and further comprising:

an extraoral segment extending to the proximal end of the tube and comprising at least one opening, wherein the extraoral segment extends externally from the mouth of the user;

an intraoral segment extending to the distal end of the tube and comprising at least one opening, wherein the intraoral segment extends into the mouth of the user and comprises a length sufficient for extending beyond a retromolar space, into the oropharynx and terminating between the posterior tongue and the soft palate; and an intermediate segment extending between the extraoral and intraoral segments and comprising a length sufficient for extending along an outside of dentitions of the user and around a rearmost dentition of the user to create a buccopharyngeal pathway of the mouth of the user;

an oxygen source comprising an outlet disposed in close proximity to the tube, allowing oxygen to flow from the outlet of the oxygen source to the tube; and a stop on the intraoral segment to secure the intraoral segment within the oropharynx against movement of the tube out of the mouth of the user.

25. The enhanced breathing device of claim 24, wherein the outlet of the oxygen source is connected to the extraoral segment.

26. The enhanced breathing device of claim 24, wherein the tube comprises a connector stem that removably connects to the outlet of the oxygen source.

27. The enhanced breathing device of claim 24, wherein an end of the oxygen source is disposed in surrounding relation to the extraoral segment of the tube.

28. The enhanced breathing device of claim 24, wherein the outlet of the oxygen source is connected to a mask that is disposed in surrounding relation to the extraoral segment of the tube.

29. The enhanced breathing device of claim 24, further comprising a stop on the tube to abut a rear molar in the mouth of the user to secure the intraoral segment within the oropharynx against movement of the tube out of the mouth of the user.

30. The enhanced breathing device of claim 24, wherein the distal end of the tube is angled to facilitate insertion of the intraoral segment into the retromolar space.

31. The enhanced breathing device of claim 24, wherein the tube comprises an outer preformed bend having a convex side and an opposite concave side.

32. The enhanced breathing device of claim 31, wherein the extraoral segment comprises an open end; the intraoral segment comprises an open end and at least one ventilation opening disposed on at least one of the convex side and the concave side of the tube; and the intermediate segment contains at least one ventilation opening disposed on at least one of an upper side between the convex and concave sides of the tube and an opposite lower side of the tube.

33. The enhanced breathing device of claim 29, wherein the stop extends beyond an adjacent periphery of the tube and is not movable.

34. A method of creating a buccopharyngeal airway in a mouth of a user, the method comprising:
providing a flexible hollow tube having a proximal end and a distal end;
positioning an extraoral segment of the tube, which extends to the proximal end of the tube and has at least one opening, exterior to the mouth of the user;
positioning an intraoral segment of the tube, which extends to the distal end of the tube and has at least one opening, beyond a retromolar space in the mouth of the user, into the oropharynx and terminating between the posterior tongue and the soft palate; and positioning an intermediate segment of the tube, which extends between the extraoral and intraoral segments, along an outside of dentitions of the user and around a rearmost dentition of the user to create the buccopharyngeal pathway of the mouth of the user.

35. The method of claim 34, further comprising securing the intraoral segment within the oropharynx.

36. The method of claim 35, wherein securing the intraoral segment within the oropharynx comprises positioning a stop in abutment with a rear molar in the mouth of the user.

37. The method of claim 34, further comprising separating at least a portion of the posterior tongue from the soft palate of the user.

38. The method of claim 37, wherein separating at least a portion of the posterior tongue from the soft palate of the user comprises positioning at least a portion of the intraoral segment between the posterior tongue and the soft palate.

39. The method of claim 34, further comprising providing an oxygen source that delivers oxygen to the tube.

40. The method of claim 39, further comprising positioning an outlet of the oxygen source in close proximity to the tube to allow oxygen to flow from the outlet of the oxygen source to the tube.

41. The method of claim 40, further comprising connecting the outlet of the oxygen source to the extraoral segment of the tube.

42. The method of claim 40, further comprising providing a connector stem on the tube and connecting the outlet of the oxygen source to the connector stem.

43. The method of claim 39, further comprising positioning an end of the oxygen source in surrounding relation to the extraoral segment of the tube.

44. The method of claim 39, further comprising connecting the oxygen source to a mask and disposing the mask in surrounding relation to the extraoral segment of the tube.

45. The enhanced breathing device of claim 24, wherein the enhanced breathing device is a medical device that enhances the breathing of the user during a medical procedure.

46. The enhanced breathing device of claim 1, wherein the enhanced breathing device is an anti-snoring device.

47. The method of claim 34, wherein the creating a buccopharyngeal airway in the mouth of the user enhances the breathing of the user during a medical procedure.

48. The method of claim 34, wherein the creating a buccopharyngeal airway in the mouth of the user is used during sleep of the user to enhance breathing of the user to reduce snoring.

49. The enhanced breathing device of claim 1, wherein the stop extends beyond an adjacent periphery of the tube.

50. The enhanced breathing device of claim 49, wherein the stop is not movable along the tube.

51. The enhanced breathing device of claim 50, wherein the tube comprises an outer preformed bend having a convex side and an opposite concave side, wherein the stop is at least partially on the concave side.

52. The enhanced breathing device of claim 9, wherein the intermediate segment comprises an additional preformed bend adjacent to the stop and to a junction between the intermediate segment and the intraoral segment.

53. The enhances breathing device of claim 52, wherein the additional preformed bend is bent at an angle between approximately 65 degrees and 135 degrees.

* * * * *

UNITED STATES PATENT AND TRADEMARK OFFICE
CERTIFICATE OF CORRECTION

PATENT NO. : 7,451,766 B2  Page 1 of 1
APPLICATION NO. : 10/816566
DATED : November 18, 2008
INVENTOR(S) : Chipp St. Kevin Miller It is certified that error appears in the above-identified patent and that said Letters Patent is hereby corrected as shown below:

On the Title Page (57) ABSTRACT, line 3    Before "an",
                         Insert --and--

(57) ABSTRACT, line 4    Delete "and intraoral",
                         Insert --an intraoral--

In the Claims

Column 14, line 63, Claim 53    Delete "enhances",
                                Insert --enhanced--

Signed and Sealed this

Nineteenth Day of May, 2009

JOHN DOLL
*Acting Director of the United States Patent and Trademark Office*